US012788879B2

(12) United States Patent
Ganesan et al.

(10) Patent No.: US 12,788,879 B2
(45) Date of Patent: Nov. 10, 2026

(54) SMART GRAVITY IV FLOW CONTROLLER

(71) Applicant: CAREFUSION 303, INC., San Diego, CA (US)

(72) Inventors: Aravinthkumar Ganesan, Coimbatore (IN); Dinesh Vattipalli, Godumakunta (IN)

(73) Assignee: CAREFUSION 303, INC., San Diego, CA (US)

( * ) Notice: Subject to any disclaimer, the term of this patent is extended or adjusted under 35 U.S.C. 154(b) by 421 days.

(21) Appl. No.: 18/504,515

(22) Filed: Nov. 8, 2023

(65) Prior Publication Data

US 2024/0157049 A1 May 16, 2024

Related U.S. Application Data

(60) Provisional application No. 63/425,257, filed on Nov. 14, 2022.

(51) Int. Cl.
*A61M 5/168* (2006.01)

(52) U.S. Cl.
CPC .... *A61M 5/16813* (2013.01); *A61M 5/16877* (2013.01)

(58) Field of Classification Search
CPC ...................... A61M 5/16813; A61M 5/16877
See application file for complete search history.

(56) References Cited

U.S. PATENT DOCUMENTS 4,018,362 A 4/1977 Ubaud
4,038,982 A 8/1977 Burke et al.
4,261,388 A 4/1981 Shelton
4,392,849 A 7/1983 Petre et al.
4,397,648 A 8/1983 Knute
4,509,943 A 4/1985 Hanzawa
4,718,896 A 1/1988 Arndt et al.
5,899,665 A 5/1999 Makino et al.
7,190,275 B2 3/2007 Goldberg et al.
8,578,785 B2 11/2013 Borenstain et al.
10,010,686 B2 7/2018 Ambrosina et al.
2018/0099090 A1 4/2018 Miyamoto
2020/0268966 A1* 8/2020 Längle .............. A61M 5/16877
2021/0018348 A1* 1/2021 Brady ........................ A61J 1/10

FOREIGN PATENT DOCUMENTS

EP 0018817 A1 11/1980

OTHER PUBLICATIONS

Davis, W. O. M., "Vascular Infusion Systems", EBME & Clinical Engineering Articles, ebme.co.uk, Copyright 1999-2024, retrieved from the internet at: https://www.ebme.co.uk/articles/clinical-engineering/vascular-infusion-systems.

(Continued)

*Primary Examiner* — Dung T Ulsh
(74) *Attorney, Agent, or Firm* — MASCHOFF BRENNAN

(57) ABSTRACT

Infusion control devices are disclosed that can actively control and monitor medical fluid administration for gravity based infusion of medical fluid, where the gravity infusion control system is couplable with an intravenous administration set and can include a flow monitor, a flow controller, and a user interface.

21 Claims, 3 Drawing Sheets

(56) References Cited

OTHER PUBLICATIONS electricaltechnology.org, "Irrigation Valve Image result for solenoid working principle", Pinterest, date unknown, retrieved from the internet at: https://www.pinterest.ca/pin/106467978672180074/.
Evelabs, "Dripo Wireless infusion monitor for gravity drips", Evelabs Technologies Private Limited, date unknown, retrieved from the internet at: https://www.evelabs.co/dripo.
Gupta, R. C. et al., "Design and implementation of controlled drug infusion system", Journal of Scientific & Industrial Research vol. 64, Oct. 2005, pp. 761-766, retrieved from the internet at: https://core.ac.uk/download/pdf/34212531.pdf.
Haasl et al., "Flow Sensor Overview", ScienceDirect Topics, 1998-2023, retrieved from the internet at: https://www.sciencedirect.com/topics/engineering/flow-sensor.
HDI Electronics, "HDI Electronics Overview", HDI Electronics SAS, date unknown, Copyright 2016, retrieved from the internet at: https://web.archive.org/web/20210312005234/http://www.hdi-electronics.fr/en/.
Kumar, P. Ravi et al., "Position Control of Servo Systems using PID Controller Tuning with Soft Computing Optimization Techniques", International Journal of Engineering Research & Technology (IJERT) vol. 3 Issue 11, Nov. 2014, ISSN: 2278-0181, retrieved from the internet at: https://www.ijert.org/research/position-control-of-servo-systems-using-pid-controller-tuning-with-soft-computing-optimization-techniques-IJERTV3IS110727.pdf.
Lötters, Joost, "MEMS flow sensors: technology, products and application the future of MEMS Chip Testing-Seminar at Salland", University of Twente, Bronkhorst High-Tech, Jun. 5, 2019, retrieved from the internet at: https://www.salland.com/wp-content/uploads/2019/07/03-Joost-Lotters-University-Twente-MEMS-Seminar-2019.pdf.
Manas Microsystems Pvt. Ltd, "Ultrasonic Flow Meters", Manas Microsystems Pvt. Ltd., date unknown, product launched 2001, retrieved from the internet at: https://www.flowmeterindia.in/ultrasonic-flow-meters.html.
New Scale Technologies, "Micro Linear Actuators", New Scale Technologies, date unknown, retrieved from the internet at: https://www.newscaletech.com/micro-motion-modules/m3-I-linear-smart-actuators/.
Shutterstock.com, "Focus on iv drip chamber and iv bag of solution with patient in Hospital" Shutterstock Stock Video ID: 1012293326, Yakuza HD, date unknown, retrieved from the internet at: https://www.shutterstock.com/video/clip-1012293326-focus-on-iv-drip-chamber-bag-solution.
Sonotec, "Ultrasonic Clamp-On Flow Meter: Sonoflow® CO.55 for Non-Contact Contamination-Free Flow Measurement on Flexible Tubes", Sonotech GmbH, Copyright 1999-2024, retrieved from the internet at: https://www.sonotec.eu/en/products/non-invasive-fluid-monitoring/flow-rate-measurement/sonoflow-clamp-on-sensor/.
Tabeebak Qatar, "Medicine and Treatments", Tabeebak Qatar, date unknown Copyright 2024, retrieved from the internet at: https://tabeebak.qa/.
Whittaker, Zack, "A widely used infusion pump can be remotely hijacked, say researchers", Biotech & Health TechCrunch, Jun. 13, 2019, Yahoo WordPress VIP, retrieved from the internet at: https://techcrunch.com/2019/06/13/alaris-infusion-pump-security-flaws/.
Win Health Medical Ltd, "Drip Assist™ Infusion Rate Monitor", Win Health Medical Ltd, (2020), retrieved from the internet at: https://web.archive.org/web/20200919100308/https://www.win-health.com/dripassist-infusion-rate-monitor.
International Search Report and Written Opinion for Application No. PCT/US2023/079422, dated Feb. 22, 2024, 11 pages.

* cited by examiner

SMART GRAVITY IV FLOW CONTROLLER

CROSS REFERENCE TO RELATED APPLICATION

This application claims priority under 35 U.S.C. § 119 to U.S. Provisional Application No. 63/425,257, entitled "Smart Gravity IV Flow Controller," filed on Nov. 14, 2022, the disclosure of which is incorporated herein by reference in its entirety.

FIELD OF THE INVENTION

The present disclosure relates generally to administration of medical fluid, such as intravenous ("IV") medical fluid therapy, and more particularly, to devices, systems, and methods, for controlling and monitoring gravity-based administration of medical fluid.

BACKGROUND

IV fluid delivery systems are used to deliver or infuse medical fluid to patients at controlled rates. Several such IV fluid delivery systems exist, including gravity-based systems that utilize the pressure of gravity to direct a medical fluid from an IV bag to a patient though tubing, and pump-based systems that use a mechanical pump that can engage tubing to direct a medical fluid from an IV bag to a patient.

Gravity-based infusion systems can include an IV administration set, which includes an IV bag, a drip chamber, infusion tubing, and a flow control device. The flow rate of the medical fluid to the patient is controlled by a flow control device, such as a linear actuator, a roller clamp, a pinch clamp, or a flow valve. Generally, the patient would receive the entire volume of medical fluid from the IV bag unless the flow is interrupted, such as by the patient or a caregiver obstructing the infusion tubing or disconnecting the infusion tubing from the patient. Pump-based infusion systems include similar components as a gravity-based infusion system; however, the flow rate and volume of medicament directed to the patient can be controlled using the infusion pump instead of a flow control device as used in gravity-based infusion systems.

SUMMARY

Although a pump-based infusion system may provide the ability to control and monitor the administration of medical fluid, such as by controlling the fluid flow rate and volume of medical fluid directed to a patient, pump-based infusion systems can be more complicated and more expensive, relative to gravity-based infusion systems. Further, gravity and pump-based infusion systems each require a caregiver or user to assemble and configure the system, including ensuring each component is prepared and appropriately connected together, and ensuring that infusion and fluid flow parameters are set as intended. Some systems, such as gravity-based infusion systems, may require the caregiver or user to prime the fluid pathway, and maintain and/or adjust the fluid flow parameters throughout the infusion. Furthermore, some infusion systems may not provide notification if a complication or error is encountered, such as flow rate irregularities, blocked filters, air in the fluid pathway or unintended disconnection of the system from the patient.

In accordance with at least some embodiments disclosed herein is the realization that, although gravity-based infusion systems may provide a lower cost alternative to pump-based infusions systems, pump and gravity-based infusion systems require a caregiver to set up, maintain, and monitor several aspects of the medical fluid administration. As such, the use of gravity-based infusion systems may expose a patient to less potential complications and errors, which may result in less incidents resulting in injury or insufficient care for a patient.

Accordingly, an aspect of the present disclosure provides a gravity infusion flow control device configured to control an IV administration set, the gravity infusion flow control device comprising a flow monitor configured to couple to the IV administration set, the flow monitor comprising a first sensor configured to detect a first flow rate of a medical fluid within a first portion of the IV administration set; and a second sensor configured to detect a second flow rate of the medical fluid within a second portion of the IV administration set; and a controller configured to receive and compare the first flow rate and the second flow rate to ensure an accurate first flow rate detected by the first sensor.

Some instances of the present disclosure provide a flow controller configured to couple to a third portion of the IV administration set, wherein the flow controller comprises an actuator and a moveable member, and wherein the actuator is configured to move the moveable member between a retracted position and an extended position. In some aspects, the moveable member is configured to change a cross-sectional area of an inner passage of the third portion of the IV administration set. In some aspects, the controller is further configured to move the moveable member between the retracted position and extended position to achieve a target flow rate of the medical fluid traveling within the IV administration set. In some aspects, the moveable member moves from the extended position toward the retracted position if the first flow rate and the second flow rate are less than the target flow rate. In some aspects, the moveable member moves from the retracted position toward the extended position if the first flow rate and the second flow rate are greater than the target flow rate.

In some aspects, the present disclosure provides that the first sensor is disposed within an IV set coupler. In some aspects, the first sensor is configured to engage the first portion of the IV administration set such that the first sensor detects a movement of the medical fluid in the first portion of the IV administration set. In some aspects, the first sensor is an optical sensor.

In some aspects, the present disclosure provides that the second sensor is configured to engage the second portion of the IV administration set such that the second sensor detects a movement of the medical fluid in the second portion of the IV administration set. In some aspects, the second sensor is an ultrasonic sensor.

In some aspects, the present disclosure provides that the gravity infusion flow control device further comprises a user interface. In some aspects, the user interface comprises a graphical user interface (GUI) configured to display information. In some aspects, the controller is further configured to transmit an error message on the GUI if the first flow rate and the second flow rate are not equal. In some aspects, the user interface comprises a speaker. In some aspects, the controller is further configured to transmit an error tone through the speaker if the first flow rate and the second flow rate are not equal.

In some aspects, the present disclosure provides that the first portion of the IV administration set is a medical fluid reservoir of the IV administering set. In some aspects, the second portion of the IV administration set is a tubing of the IV administering set. In some aspects, the second portion of the IV administration set is located downstream from the first portion of the IV administration set.

Accordingly, the present application addresses several operational challenges encountered in prior systems and methods for administering medical fluids using gravity-based infusion systems and provides numerous improvements for controlling and monitoring medical fluid administration, which can provide patient protection from complications during infusion therapy, improve workflow for clinicians and caregivers, maintain patient mobility, reduce medication administration errors, increase medication security, increase medication delivery accuracy and rate stability, lower costs, and increase documentation efficiency, as well as preventing, detecting, and resolving complications such as, an occlusion, extravasation, and air in the fluid pathway.

Features of the present Application can provide gravity infusion control systems that can permit control of aspects including, but not limited to, any of fluid flow rate, dosage volume, priming of the IV administration set, and automatically stopping and/or starting infusion. Further, aspects of the present Application can provide monitoring of aspects of the fluid pathway of the IV administration set including, but not limited to, pressure, fluid flow rate, occlusions, the presence of air, fluid flow rate, leakage, infiltration, and the potential occurrence of tampering to the IV administration set.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

DETAILED DESCRIPTION

Figure 1A:
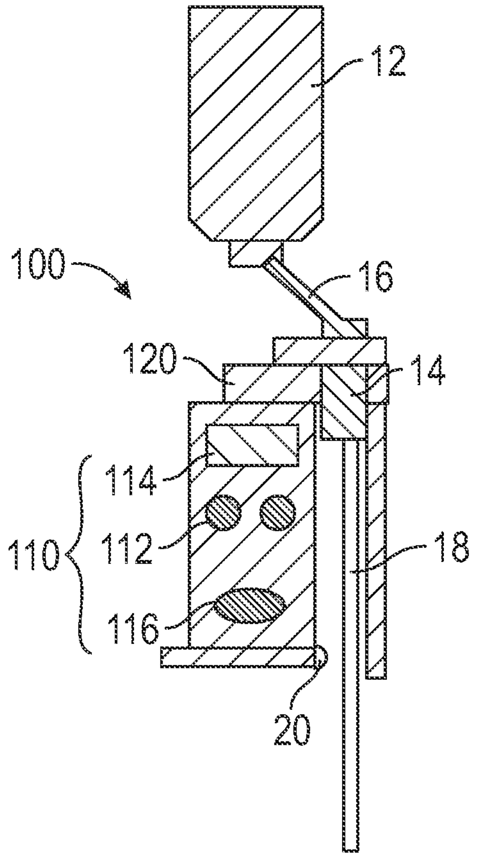
FIG. 1A illustrates a gravity infusion control system in use with an IV administration set, in accordance with aspects of the present disclosure.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of an IV administration set, such embodiments can be used in other fluid conveyance systems. Furthermore, various applications of such embodiments and modifications thereto, which may occur to those who are skilled in the art, are also encompassed by the general concepts described herein.

In accordance with some embodiments, the present application discloses various features and advantages of a gravity infusion control system. The gravity infusion control system can provide for provides numerous improvements for controlling and monitoring medical fluid administration. The gravity infusion control system can monitor and control aspects of medical fluid administration using an IV administration set, and can prevent, detect, and resolve potential or actual complications associated with the medical fluid administration.

The gravity infusion control system includes a user interface, a flow monitor, and a flow controller. The user interface permits a user to set and/or adjust operational characteristics of the gravity infusion control system, including, but not limited to, dosage and/or volume of medical fluid to be directed to a patient, flow rate of the medicament, start and/or stop parameters for the medical fluid administration, and priming of the fluid pathway for the medical fluid. The user interface, in some embodiments of the present disclosure, can include a graphical user interface.

The user interface can be incorporated into a housing having any of the flow detection and flow controllers; however, in some embodiments, the user interface can be located separately from the housing, such as on a separate remote control or mobile device. In some embodiments of the present disclosure, a user interface can be incorporated into the housing and another user interface can be separately located on a remote control or a mobile device.

The flow monitor permits the gravity infusion control system to couple with a medical fluid reservoir or container, and to detect the occurrence of flow from or through the medical fluid reservoir. The flow monitor includes an IV administration set coupler that is configured to engage against or retain a portion of an IV administration set forming a medical fluid reservoir, such as a drip chamber. The flow monitor also includes one or more flow sensors configured to detect any of a change in mass or movement of the medical fluid reservoir to determine the occurrence of flow from or through the medical fluid reservoir. In some embodiments of the present disclosure, the one or more flow sensors can comprise any of a drop sensor, a weight change sensor, an ultrasonic sensor, a photovoltaic sensor, a photoelectric sensor and/or an optical sensor.

The flow controller permits the gravity infusion control system to couple with a portion of an IV administration set forming an inner passage for fluid flow, and to control a rate of fluid flow through the inner passage. The flow controller includes fluid control device that is configured to engage against or retain a portion of an IV administration set forming an inner passage, such as the IV tubing. To control a rate of fluid flow through the inner passage, the IV administration set coupler for the flow controller includes a moveable member or surface that can engage against the IV tubing or against a flow control device of the IV administration set. Engagement of the movable member against the IV tubing or flow control device can cause a change in the cross-sectional area of the inner passage, thereby resisting flow therethrough. In some embodiments, the flow controller can be controlled remotely by a user or caregiver's using a mobile device or remote.

The gravity infusion control system can be configured such that the flow monitor comprises an IV administration set coupler, and the flow controller comprises a movable part capable of extending and retracting to engage the IV tubing. However, it should be understood that the present disclosure contemplates embodiments in which the flow monitor and the flow controller comprise multiple IV administration set couplers.

Figure 1B:
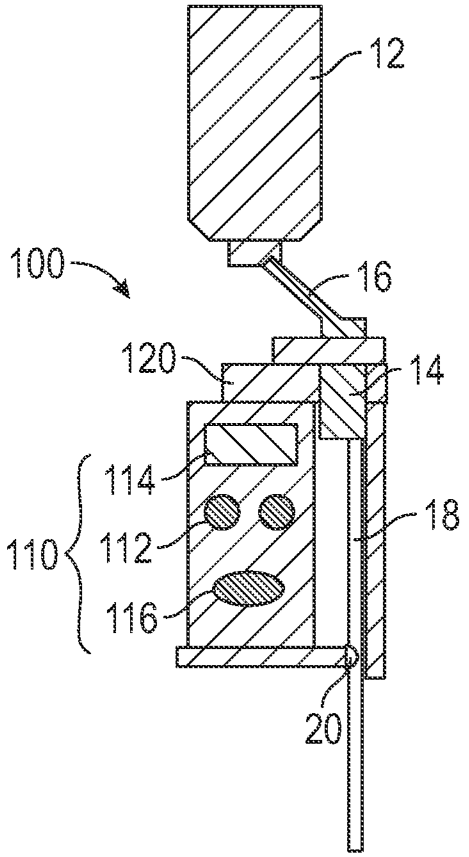
FIG. 1B illustrates a gravity infusion control system in use with an IV administration set, in accordance with aspects of the present disclosure.
Figure 2:
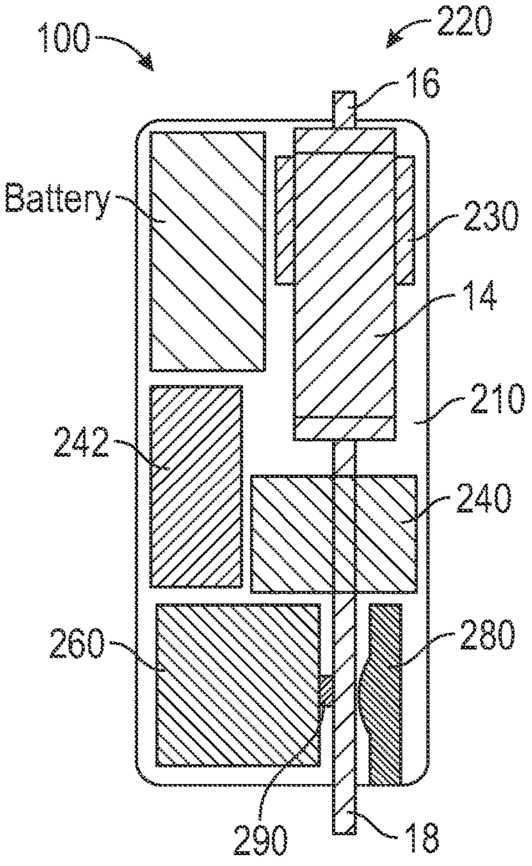
FIG. 2 illustrates a front detail view of a gravity infusion control system, in accordance with aspects of the present disclosure.

Referring to FIGS. 1-2, an embodiment of a gravity infusion control system 100 is illustrated in use with an IV administration set. The gravity infusion control system 100 includes a user interface, a flow monitor, and a flow controller.

The gravity infusion control system 100 is coupled with an IV administration set having an IV bag 12 and a drip chamber 14 fluidly coupled together by IV tubing 16 extending therebetween. A flow control device 20 is located proximate the drip chamber 14 and is configured to contact a length of IV tubing 18 extending between the drip chamber 14 and a patient. The IV tubing 18 may be intravenously coupled to the patient through a catheter. The IV administration set and the gravity infusion control system 100 are arranged together, with the drip chamber 14 coupled to the IV administration set coupler 120.

The IV bag 12 may be suspended, the drip chamber 14 may be inserted into the IV administration set coupler 120, and the flow control device 20 may be located proximate the drip chamber 14 along the IV tubing 18. A processor of the gravity infusion control system 100 can determine if there is air in the inner passage of the IV administration set, which can be displayed by a graphical user interface 114. After coupling the IV tubing 18 of the IV administration set to the patient, a combination of buttons 112, graphical user interface 114 and speaker 116 of the user interface 110 can be used to start the infusion process. Starting the infusion process can include entering operation parameters, such as a fluid flow rate for the medical fluid and a volume of medical fluid to be administered.

The gravity infusion control system 100 can also receive, transmit, and save data and/or documentation related to any of the patient identity, the medicament or medical fluid, and the infusion parameters. Further, the gravity infusion control system 100 can monitor and control the infusion process by preventing, detecting, and resolving complications such as an occlusion, extravasation, and air in the fluid pathway.

Figure 3:
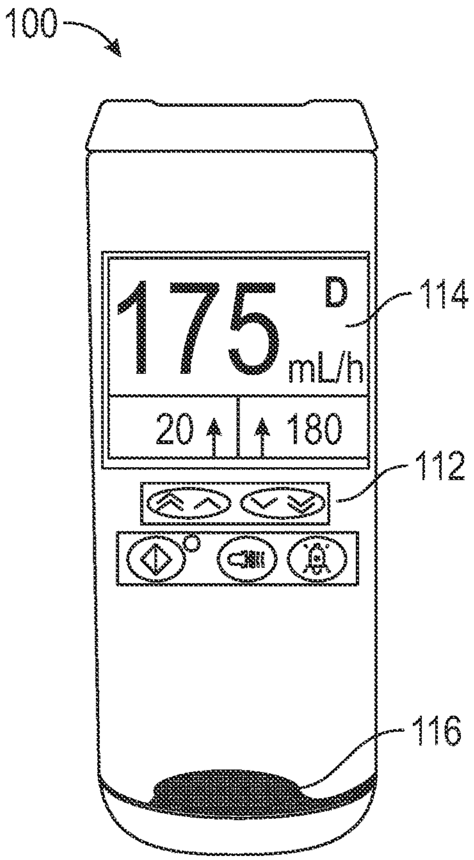
FIG. 3 illustrates a front view of a gravity infusion control system, in accordance with aspects of the present disclosure.

Referring now to FIG. 3, the flow monitor may include an IV administration set coupler 120 (not shown) configured to engage against or retain a medical fluid reservoir of the IV administration set, such as the drip chamber 14. In some embodiments of the present disclosure, the flow monitor is configured to couple with one or more medical fluid reservoir of the IV administration set.

To permit coupling with a drip chamber 14, a housing 210 of the gravity infusion control system 100 can form at least a portion of the IV administration set coupler 120 for the flow monitor. The housing 210 can define a slot or channel 220 configured to receive the drip chamber 14 and at least a portion of the IV tubing 18 therein.

When coupled with the IV administration set, the flow monitor can identify the presence of fluid flow from the medical fluid reservoir of the IV administration set. To identify the presence of fluid flow from an IV bag 12, a drip chamber 14, or another medical fluid reservoir of the IV administration set, the flow monitor includes an optical sensor 230 coupled to the IV administration set coupler 120. In some embodiments, the optical sensor 230 is disposed within the IV administration set coupler 120. The optical sensor 230 may include a sensor to detect movement within the medical fluid reservoir. In some embodiments, the optical sensor 230 can be a photovoltaic sensor configured to detect a drop of liquid traveling through the drip chamber 14. As part of a mistake-proofing system of the gravity infusion control system, to confirm the fluid flow from a drip chamber 14, or another medical fluid reservoir of the IV administration set, the flow monitor further includes an ultrasonic sensor 240 located along IV tubing 18 within the channel 220 proximate the IV administration set coupler 120. The ultrasonic sensor 240 can include any of a sensor to detect movement or a of a medical fluid within the IV tubing 18. In some embodiments, the ultrasonic sensor 240 can be configured to detect a change of volume traveling through the IV tubing 18.

The flow controller of the gravity infusion control system can include the flow control device 20 that is configured to control a rate of fluid flow through the IV administration set. The flow control device 20 can control the rate of fluid flow through the IV administration set by engaging against the IV tubing 18 of the IV administration set, where the flow control device 20 of the IV administration set can be any of, but not limited to, a servo based linear actuator, a cylindrical clamp, a roller clamp, a pinch clamp, or another device configured to change a rate of fluid flow through the inner passage of the IV tubing 18. In some embodiments of the present disclosure, the flow control device 20 for the flow controller can cause a change the cross-sectional area of the inner passage of the IV tubing 18.

To control the rate of fluid flow through the IV administration set, the flow control device 20 includes a moveable member, e.g., knob 290, that engages against the IV tubing 18 in an extended position. The moveable member of the flow control device 20 can cause the IV tubing 18 to engage against an opposite surface 280 of the channel 220, as illustrated in FIG. 2. The flow control device 20 can cause the knob 290 to move. As the knob 290 of the flow control device 20 moves from a retracted position to an extended position, the IV tubing 18 that extends between the knob 290 and the opposite surface 280 becomes compressed or squeezed, thereby changing a cross-sectional area of the inner passage of the IV tubing 18.

To orient the flow control device with the IV tubing 18, the flow controller can include an alignment and/or retaining mechanism. The alignment and/or retaining mechanism can be configured to ensure the IV tubing 18 will be engaged by the knob 290 of the flow control device 20 when moving from the retracted position to the extended position. Further, the alignment and/or retaining mechanism can retain the flow control device in an intended position within the flow controller.

In some embodiments of the present disclosure, the knob 290 engages directly against the IV tubing 18 to cause a length of IV tubing 18 to be compressed to resist fluid flow therethrough, as illustrated in the gravity infusion control system of FIGS. 1-2. Conversely, movement of the knob 290 from the extended position to the retracted position can cause the IV tubing 18 to expand to an unrestrained position thereby reducing resistance to fluid therethrough.

Upon completion of the infusion process, the flow controller can cause the flow control device 20 to obstruct the inner passage of the IV administration set, such as by fully closing the cross-sectional area of the IV tubing 18. In some embodiments of the present disclosure, the flow controller can restrict the inner passage of the IV administration set to obstruct fluid flow therethrough upon identification of a complication such as a leak.

The IV administration set may be coupled to the gravity infusion control system 100 by positioning the drip chamber 14 or other medical fluid reservoir in a channel of a flow monitor, and inserting the IV tubing 18 through a passage of the flow controller. To control a rate of fluid flow through the IV tubing 18, the movable member can cause a length of IV tubing 18 to be compressed to resist fluid flow therethrough.

The user interface 110 of the gravity infusion control system is configured to permit a user to set and/or adjust operational characteristics of the system and infusion process. The user interface 110 can include one or more buttons 112 or another device, such as a dial, switch, knobs, or the like, to interact with, control, and monitor the gravity infusion control system. The buttons 112 may allow the user to set at least a target flow rate or a target delivery volume.

In some embodiments of the present disclosure, the gravity infusion control system 100 can include a graphical user interface (GUI) 114. The graphical user interface 114 can display data and information regarding the system and operational characteristics of the infusion process. In some embodiments, the graphical user interface 114 can be configured as a touch screen display that can permit a user to interact with the gravity infusion control system by touching areas on the touch screen display. In some embodiments of the present disclosure, the gravity infusion control system 100 can include a speaker 116. The speaker 116 can be configured to produce a tone or sound or combination of tones or sounds that can be heard by a user or caregiver.

The controller 250 of the gravity infusion control system may provide a function for receiving various signal inputs from the sensors and transmitting signal outputs necessary to use a gravity infusion control system according to various aspects of the subject technology. The controller 250 according to an exemplary embodiment of the present disclosure may include a processor (e.g., computer, microprocessor, CPU, application-specific integrated circuit ("ASIC"), circuitry, logic circuits, etc.). The memory may be implemented by a non-transitory memory storing, for example, a program(s), software instructions, reproducing algorithms, etc., which, when executed, transmits and received information, and a processor may be configured to execute the program(s), software instructions, reproducing algorithms, etc. Herein, the memory and the processor me be implemented as separate semiconductor circuits. Alternatively, the memory and processor may be implemented as a single integrated semiconductor circuit. The processor may embody one or more processors. The associated non-transitory memory storing software instructions, which, when executed by the processor of the controller 250, provides a function for transmitting and receiving information necessary to control fluid flow within the IV administration set and identify irregularities in the operation of a gravity infusion control system.

The system may identify the irregularity by comparing signal 410 and signal 420. Signal 410 and signal 420 (both measuring the flow rate of the fluid traveling through the IV tubing 16, 18) are expected to match under normal conditions. If signal 410 and signal 420 match, then no irregularity (at least initially) may be determined. If signal 410 and signal 420 do not match, then an irregularity may be determined. For example, signal 410 may be from an optical sensor 230 on the drip chamber 14, and signal 420 may be from an ultrasonic sensor 240 on the IV tubing 18. If the signal from the optical sensor 230 does not match with the signal from the ultrasonic sensor 240, then the system may detect an irregularity. Also, if one or more of signal 410 and signal 420 are not available, the system may determine a system fault and provide an alarm and/or perform diagnostic measures to determine whether the signal failure can be identified and corrected.

If signal 410 and signal 420 do match, but do not equal a target flow rate entered by a user or caregiver on the user interface 110, the controller can perform flow control in order to reduce or increase the flow rate of liquid in the IV tubing 18. If signal 410 and signal 420 indicate that the measured fluid flow rate in the IV tubing 18 is greater than the target flow rate, the controller 250 may cause the knob 290 of the flow control device 20 to move from the retracted position to the extended position, thereby decreasing the cross-sectional area of the inner passage of the IV tubing 18. However, in order to achieve the target flow rate, the controller 250 may cause the knob 290 to stop partially between the retracted position and the extended position. If signal 410 and signal 420 indicate that the measured flow rate in the IV tubing 18 is less than the target flow rate, the controller 250 may cause the knob 290 of the flow control device 20 to move from the extended position to the retracted position, thereby increasing the cross-sectional area of the inner passage of the IV tubing 18. However, in order to achieve the target flow rate, the controller may cause the knob 290 to stop partially between the extended position and the retracted position.

Figure 4:
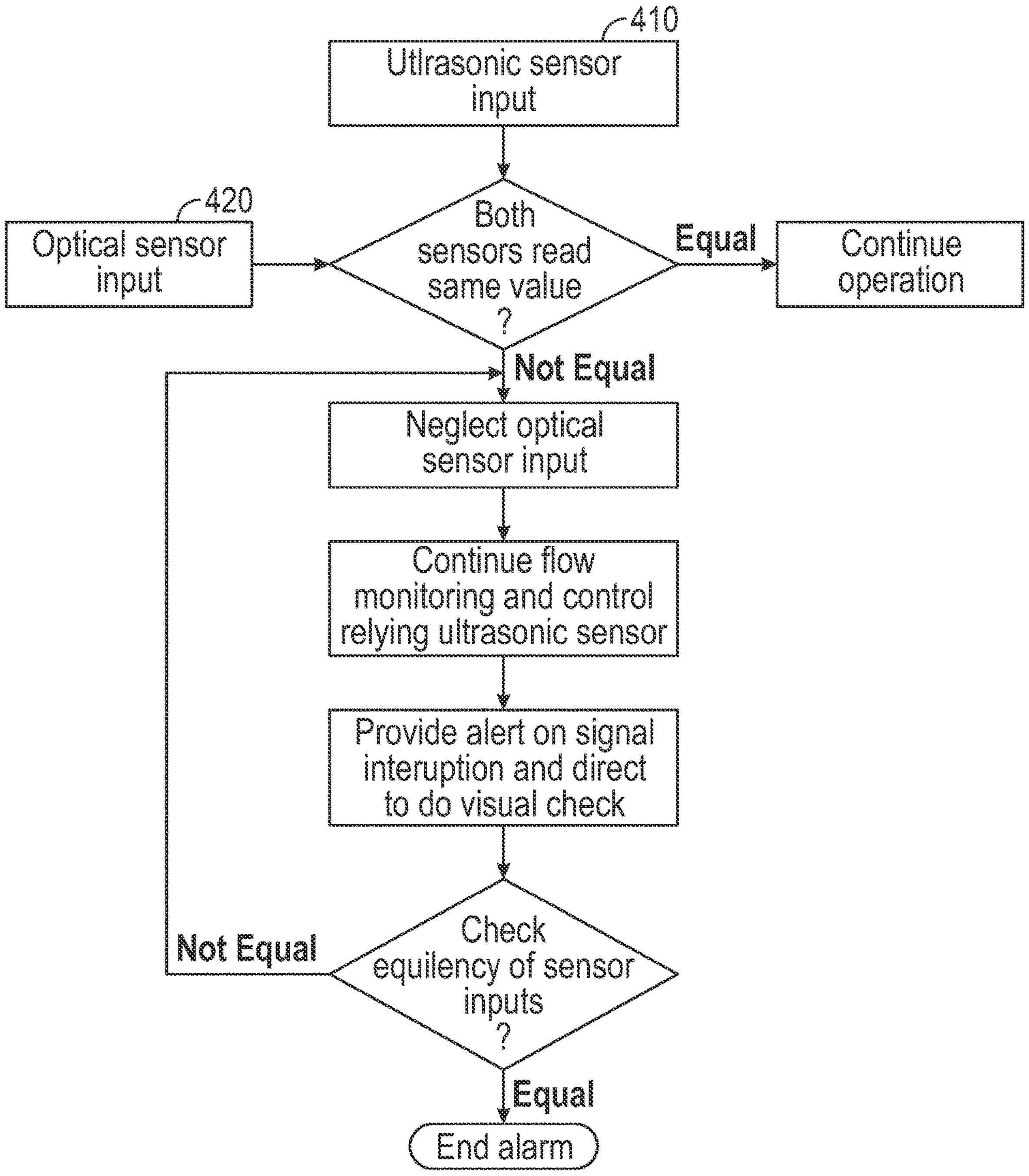
FIG. 4 is a flowchart illustrating a method of controlling a gravity infusion control system, in accordance with aspects of the present disclosure.

FIG. 4 depicts an example flow diagram for a mistake-proofing feature of controller 250 of the gravity infusion control system, according to various aspects of the subject technology. According to various implementations, the controller 250 receives signal 410 indicative of the ultrasonic sensor 240 input and signal 420 indicative of the optical sensor 230 input. If signal 410 and signal 420 are equal, the controller 250 continues operation of the gravity infusion control system. If signal 410 and signal 420 are not equal, suggesting an irregularity, the controller will produce an error on the graphical user interface 114. The error may be an error message displayed on the graphical user interface 114 and/or an error tone transmitted through the speaker 116. Upon detection of an irregularity, the controller 250 will neglect the input from the optical sensor 230 in favor of the input from the ultrasonic sensor 240. The controller 250 will periodically compare signal 410 and signal 420 to determine the continued existence of the irregularity. This periodic comparison period may be, for example, every 15 seconds. Once the controller 250 determines that the values of signal 410 and signal 420 are equal, the error will end.

The controller 250 also couples the gravity infusion control system 100 to a network (not shown) through network interfaces. Network interfaces may include, e.g., a wireless access point (e.g., Bluetooth or WiFi) or radio circuitry for connecting to a wireless access point. Network interfaces may also include hardware (e.g., Ethernet hardware) for connecting the gravity infusion control system to a part of a network of computers such as a local area network ("LAN"), a wide area network ("WAN"), wireless LAN, or an Intranet, or a network of networks, such as the Internet. Any or all components of the controller 250 can be used in conjunction with the subject disclosure. Such coupling of the gravity infusion control system to a network may allow remote monitoring and control of the gravity infusion control system by a user or caregiver.

The gravity infusion control system of the present disclosure can further provide features directed to detecting potential or actual complications related to the infusion process. In some embodiments, the gravity infusion control system can provide systems or sub-systems configured to identify potential complications related to the fluid pathway, including, but not limited to, an occlusion, air in the fluid pathway, a leak or extravasation of the fluid pathway, and instability in the medical fluid flow. To detect potential or actual complications, the gravity infusion control system can include a sensor, such as an air-in-line sensor, a weight sensor, and/or a pressure sensor.

In some embodiments of the present disclosure, the gravity infusion control system is configured to be couplable with one or more sub-system or module, such as an air-in-line subsystem, a tamper-proof subsystem, an infiltration subsystem, a leak detection subsystem, a pressurization subsystem, and/or a patient data subsystem.

The gravity infusion control system can provide a workflow having increased efficiency and reliability, relative to other infusion systems. A workflow associated with the gravity infusion control system can include, but is not limited to a preparation stage, a priming stage, an infusion stage, an infusion maintenance stage, and an infusion conclusion stage. It should be understood that one or more stages can occur concurrently or sequentially.

During a preparation stage of the workflow, a caregiver can scan a patient wristband to for identification and verification of the patient. During a priming stage, a caregiver can place an IV administration set in the gravity infusion control system and initiate priming of the fluid pathway. The priming stage may also include indication, by the gravity infusion control system, that there is no complication present, such as air in the fluid pathway. During the infusion stage, the caregiver can enter a target fluid drop rate and initiate or start the infusion process. The infusion stage, or any other stage, can initiate the saving of documentation or data associated with the infusion process. During an infusion maintenance stage, the gravity infusion control system can provide one or more notification, such as the presence of an occlusion, air-in-line, tampering, leakage, and/or infiltration. Further, during the infusion maintenance stage, the gravity infusion control system can automatically maintain the rate of fluid flow. During an infusion conclusion stage, the gravity infusion control system can automatically clamp or obstruct the fluid pathway of the IV tubing, thereby preventing further medical fluid delivery or unintended leakage of medical fluid during disconnection of the IV administration set from the patient.

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A gravity infusion flow control device configured to control an IV administration set, the gravity infusion flow control device comprising:

a flow monitor configured to couple to the IV administration set and comprising a first sensor, and a second sensor, the first sensor configured to detect a first flow rate of a medical fluid within a first portion of the IV administration set, and the second sensor configured to detect a second flow rate of the medical fluid within a second portion of the IV administration set; and a controller configured to receive and compare the first flow rate and the second flow rate to ensure an accurate first flow rate detected by the first sensor, wherein, if the first flow rate and the second flow rate are not equal, the controller is configured to produce an error, neglect an input from the first sensor, and accept an input from the second sensor.

2. The gravity infusion flow control device of claim 1, further comprising a flow controller configured to couple to a third portion of the IV administration set.

3. The gravity infusion flow control device of claim 2, wherein the flow controller comprises an actuator and a moveable member, wherein the actuator is configured to move the moveable member between a retracted position and an extended position.

4. The gravity infusion flow control device of claim 3, wherein the moveable member is configured to change a cross-sectional area of an inner passage of the third portion of the IV administration set.

5. The gravity infusion flow control device of claim 4, wherein the controller is further configured to move the moveable member between the retracted position and extended position to achieve a target flow rate of the medical fluid traveling within the IV administration set.

6. The gravity infusion flow control device of claim 5, wherein the moveable member moves from the extended position toward the retracted position if the first flow rate and the second flow rate are less than the target flow rate.

7. The gravity infusion flow control device of claim 5, wherein the moveable member moves from the retracted position toward the extended position if the first flow rate and the second flow rate are greater than the target flow rate.

8. The gravity infusion flow control device of claim 1, wherein the first sensor is disposed within an IV set coupler.

9. The gravity infusion flow control device of claim 8, wherein the first sensor is configured to engage the first portion of the IV administration set such that the first sensor detects a movement of the medical fluid in the first portion of the IV administration set.

10. The gravity infusion flow control device of claim 9, wherein the first sensor is an optical sensor.

11. The gravity infusion flow control device of claim 1, wherein the second sensor is configured to engage the second portion of the IV administration set such that the second sensor detects a movement of the medical fluid in the second portion of the IV administration set.

12. The gravity infusion flow control device of claim 11, wherein the second sensor is an ultrasonic sensor.

13. The gravity infusion flow control device of claim 1, wherein the gravity infusion flow control device further comprises a user interface.

14. The gravity infusion flow control device of claim 13, wherein the user interface comprises a graphical user interface (GUI) configured to display information.

15. The gravity infusion flow control device of claim 14, wherein the controller is further configured to transmit an error message on the GUI if the first flow rate and the second flow rate are not equal.

16. The gravity infusion flow control device of claim 13, wherein the user interface comprises a speaker.

17. The gravity infusion flow control device of claim 16, wherein the controller is further configured to transmit an error tone through the speaker if the first flow rate and the second flow rate are not equal.

18. The gravity infusion flow control device of claim 1, wherein the first portion of the IV administration set is a medical fluid reservoir of the IV administering set.

19. The gravity infusion flow control device of claim 18, wherein the second portion of the IV administration set is a tubing of the IV administering set.

20. The gravity infusion flow control device of claim 1, wherein the second portion of the IV administration set is located downstream from the first portion of the IV administration set.

21. A gravity infusion flow control device configured to control an IV administration set, the gravity infusion flow control device comprising:

a flow monitor configured to couple to the IV administration set, the flow monitor comprising a first sensor, and a second sensor, the first sensor configured to detect a first flow rate of a medical fluid within a first portion of the IV administration set, and the second sensor configured to detect a second flow rate of the medical fluid within a second portion of the IV administration set;

a flow controller comprising a moveable member configured to move between a retracted position and an extended position to couple to a third portion of the IV administration set; and a controller configured to:

receive and compare the first flow rate and the second flow rate to ensure an accurate first flow rate detected by the first sensor, wherein, if the first flow rate and the second flow rate are not equal, the controller is configured to produce an error, neglect an input from the first sensor, and accept an input from the second sensor, and move the moveable member between the retracted position and extended position to achieve a target flow rate of the medical fluid traveling within the IV administration set by changing a cross-section area of an inner passage of the third portion of the IV administration set.

* * * * *